US006264996B1

(12) United States Patent
Braswell et al.

(10) Patent No.: US 6,264,996 B1
(45) Date of Patent: Jul. 24, 2001

(54) COMPOSITION FOR INHIBITING PRODUCTION OF DIHYDROTESTOSTERONE TO TREAT BENIGN PROSTATE HYPERPLASIA

(75) Inventors: A. Glenn Braswell, Atlanta, GA (US); Aftab J. Ahmed, Marina Del Rey, CA (US)

(73) Assignee: Glenn A. Braswell, Miami, FL (US)

( * ) Notice: Subject to any disclaimer, the term of this patent is extended or adjusted under 35 U.S.C. 154(b) by 0 days.

(21) Appl. No.: 08/989,161

(22) Filed: Dec. 11, 1997

(Under 37 CFR 1.47)

Related U.S. Application Data

(60) Provisional application No. 60/032,392, filed on Dec. 11, 1996.

(51) Int. Cl.$^7$ .................................................. A61K 35/78
(52) U.S. Cl. ........................... 424/727; 424/728; 424/450
(58) Field of Search .................................. 424/195.1, 450

(56) References Cited

U.S. PATENT DOCUMENTS

| | | | |
|---|---|---|---|
| 4,752,425 | 6/1988 | Martin et al. | 264/4.6 |
| 5,227,170 | 7/1993 | Sullivan | 424/450 |
| 5,534,499 | * 7/1996 | Ansell | 514/25 |
| 5,567,433 | 10/1996 | Collins | 424/450 |

OTHER PUBLICATIONS

Champault et al., Br. J. clin. Pharmac. 18: 461–462 (1984).*
Braeckman, Current Therapeutic Research 5597): 776–785 (Jul. 1994).*
Dallob et al., The Effect of Finasteride, a 5α–Reductase Inhibitor on Scalp Skin Testosterone and Dihydrotestosterone Concentrations in Patient with Male Pattern Baldness, Journal of Clinical Endocrinology and Metabolism, 1994, vol. 79, No. 3, pp. 703–706.
R.S. Rittmaster, Finasteride, The New England Journal of Medicine, Jan. 13, 1994, vol. 330, No. 2, pp. 120–125.
Sultan et al., Inhibition of Androgen Metabolism and Binding by a Liposterolic Extract of "Serenoa Repens B" In Human Foreskin Fibroblasts, J. Steroid Biochem., vol. 20, No. 1, pp. 515–519, 1984.
Casarosa et al., Lack of Effects of a Lyposterolic Extract of *Serenoa repens* on Plasma Levels of Testosterone, Follicle–Stimulating Hormone, and Luteinizing Hormone, Clinical Therapeutics, vol. 10, No. 5, 1988, pp. 585–588.
J. Braeckmann, The extract of *Serenoa repens* in the treatment of behighn prostatic hyperplasia: A multicenter open study, The American Journal of Natural Medicine, Nov. 1994, Curr Ther Res 55: 776–85.
F. DiSilverio et al., Evidence that *Serenoa repens* extract displays an antiestrogenic activity in prostatic tissue of benigh prostatic hypertrophy patients, Eur Urol vol. 21, pp. 309–314, 1992.
FO–TI (Raw and Cured).
Xiao et al., Immunological Aspects of Chinese Medicianl Plants as Antiageing Drugs, Journal of Ethnopharmacology, vol. 38, 1993, pp. 167–175.
Hong et al., Astragalus Membranaceus and Polygonum Multiflorum Protect Rat Heart Mitochondria Against Lipid Peroxidation, American Journal of Chinese Medicine, 1994, vol. XXII, No. 1, pp. 63–70.
Precious Prescriptions, Tonic Herbs and Formulas.
Herbs that Tonify the Blood.
What is SHEN MIN?, Brotech Corporation.
Saw Palmetto, Smart Basics Catalog.
Herbal Materia Medica, Saw Palmetto.
Russell and Wilson, Annual Review of Biochemistry, vol. 63, p. 21 (1994).

* cited by examiner

*Primary Examiner*—Jean C. Witz
(74) *Attorney, Agent, or Firm*—Sierra Patent Group, Ltd.

(57) ABSTRACT

A pharmaceutical composition containing a dihydrotestosterone blocker of a 5α-reductase active site binding peptide, Serenoa repens, or mixtures thereof, encapsulated within liposomes, and a pharmaceutically acceptable carrier is described. The composition is preferably orally administered in amounts effective to block production of excessive amounts of dihydrotestosterone (DHT) in prostatic tissue. By doing so, the composition is able to prevent and treat disorders of the prostate, including benign prostate hyperplasia.

14 Claims, No Drawings

COMPOSITION FOR INHIBITING PRODUCTION OF DIHYDROTESTOSTERONE TO TREAT BENIGN PROSTATE HYPERPLASIA

This nonprovisional application claims the benefit of U.S. Provisional Application No. 60/032,392. filed Dec. 11, 1996.

BACKGROUND OF THE INVENTION

1. Field of the Invention

This invention relates to a composition containing compounds which inhibit the reduction of testosterone to dihydrotestosterone (DHT) in prostate tissue. The composition is used to prevent excessive levels of DHT in prostate tissue, a major contributing cause of benign prostate hyperplasia (BPH).

2. Discussion of Related Art

Benign prostate hyperplasia (BPH) in mammals, particularly human males, is known to result from prolonged accumulation of testosterone in the prostate. The testosterone is converted in prostatic tissue to a more potent metabolite dihydrotestosterone (DHT). DHT stimulates cellular proliferation in the prostatic tissue, causing enlargement of the prostate.

DHT is produced in a mammal by the reduction of testosterone. Testosterone is bound to the enzyme 5α-reductase through recognition of a specific sequence of amino acids in the reductase, the active site of the enzyme with respect to testosterone. The testosterone is then reduced to DHT. There are two isoforms of 5α-reductase in mammals, particularly humans. Type 1 of the enzyme is found predominantly in scalp skin, while type 2 is found predominantly in the prostate. See, for example, Rittmaster, "Finasteride", The New England Journal of Medicine, vol. 330, no. 2, pps. 120–125 (1994).

In the prostate, DHT has a "normal" base level in mammals in order to properly stimulate cellular proliferation within the prostate and to undertake other reported physiological roles. When the DHT levels exceed the base level, excessive cellular proliferation begins, accompanied by prostate enlargement.

Finasteride is a 5α-reductase inhibitor, approved by the FDA, that has been studied extensively in mammalian, including human, subjects with respect to its ability to treat BPH. Finasteride is a steroid exhibiting an ability to reduce the activity of reductase, particularly the type 2 5α-reductase. If the enzyme activity is reduced, testosterone present in the prostate, particularly excess testosterone, will not be converted to DHT to create excess DHT in the prostatic tissue.

Other studies have determined that Serenoa repens, also known as saw palmetto, which is from berries of the palmetto palm tree, has an antiandrogenic and antiestrogenic activity in prostatic tissue. See, for example, Sultan et al., "Inhibition of Androgen Metabolism and Binding by a Liposterolic Extract of 'Serenoa Repens B' in Human Foreskin Fibroblasts", J. Steroid Biochem., vol. 20, no. 1, pps. 515–519 (1984) and DiSilverio et al. "Evidence That Serenoa Repens Extract Displays an Antiestrogenic Activity in Prostatic Tissue of BPH Patients", Eur. Urol., vol. 21, pps. 309–314 (1992).

SUMMARY OF THE INVENTION

It is an object of the present invention to develop a pharmaceutical composition that can effectively inhibit the production of DHT from 5α-reductase in prostatic tissue. It is a further object of the present invention to develop a method of administering the composition so that the composition can be used in maintaining normal base levels of DHT in prostatic tissue, thereby treating prostate disorders including BPH. It is a still further object of the present invention to develop a method of delivering the pharmaceutical composition specifically to prostatic tissue of the patient.

These and other objects are achieved by a pharmaceutical composition containing compounds capable of blocking production of DHT in prostatic tissue. The DHT blockers are preferably encapsulated in liposomes. In addition to the DHT blockers, the composition includes a pharmaceutically acceptable carrier. Polygonum multiflorum is also preferably included in the composition.

The invention also includes a method of administering the composition to a mammal in a manner effective to block the production of DHT in prostatic tissue of the mammal. In the method, the composition is preferably administered orally, although topical administration is also possible.

DETAILED DESCRIPTION OF PREFERRED EMBODIMENTS

The pharmaceutical composition of the invention includes as an active ingredient a DHT blocker of a 5α-reductase active site binding peptide, Serenoa repens, or mixtures thereof. By "DHT blocker" is meant a compound that inhibits or decreases the activity of 5α-reductase so as to hinder and/or block the reduction of testosterone to DHT.

By "5α-reductase active site binding peptide" is meant a peptide having a sequence of amino acids that specifically bind to the active site of 5α-reductase. The active site of the reductase enzyme is that sequence of amino acids in the enzyme that are recognized by testosterone and to which testosterone binds in its reduction to DHT. The DNA sequences of both types of 5α-reductase have been determined and published. See, for example, Russell and Wilson, Annual Review of Biochemistry, vol. 63, p. 21 (1994). To bind to the active site of the enzyme, the peptide should have a three-dimensional physiological conformation corresponding as closely as possible to the conformation of the enzyme, both of which may be modeled by commercially available software as understood by one of skill in the art.

By binding the peptide to the active site of the 5α-reductase, testosterone is then unable to bind to the enzyme present in prostatic tissue, and therefore unable to be reduced to DHT. In this manner, the presence of DHT in the prostate may be regulated and maintained at desired normal base levels. The dosage level of the DHT blocker must be responsibly set so that DHT levels are not reduced beyond the normal base level of the patient.

Any suitable peptide having an amino acid sequence in the chain that is capable of specifically binding to the active site of the reductase enzyme may be used. Preferably, the peptide contains a pentapeptide sequence as NH3-Xaa-Xaa-Xaa-Xaa-Xaa-COO-, wherein Xaa is an amino acid chosen from serine, asparagine, alanine, threonine, glutamic acid and aspartic acid (SEQ ID NO. 7). Examples of the most preferred sequences are:

+NH3-Serine-Serine-Asparagine-Alanine-Threonine-COO-(SEQ ID NO. 1)

+NH3-Asparagine-Serine-Asparagine-Alanine-Threonine-COO-(SEQ ID NO. 2)

+NH3-Asparagine-Threonine-Asparagine-Alanine-Threonine-COO-(SEQ ID NO. 3)

+NH3-Asparagine-Serine-Glutamic Acid-Alanine-Threonine-COO-(SEQ ID NO. 4)

+NH3-Asparagine-Serine-Asparagine-Aspartic Acid-Threonine-COO-(SEQ ID NO. 5)

+NH3-Asparagine-Serine-Asparagine-Alanine-Serine-COO-(SEQ ID NO. 6).

The peptide DHT blocker may be synthesized according to the usual methods of solution and solid phase peptide chemistry, or by classical methods known in the art. The solid-phase procedure is well known in the art and has been described by Stewart and Young, Solid Phase Peptide Synthesis: Second Ed. (Pierce Chemical Co., Rockford, Ill. 1984). Such method uses supporting resins to which the starting amino acid is bound, and the desired sequence is built using solutions of the amino acids with appropriate, known activators. Solution methods which can be employed to synthesize the peptide sequence are set forth in Bodansky et al., Peptide Synthesis, 2nd Edition, John Wiley & Sons, New York, N.Y. 1976. Another method of forming a peptide sequence is described in WO 92/10709.

The amino acids are readily available from numerous sources.

The DHT blocker may also comprise Serenoa repens extract (SRE), also commonly known as saw palmetto. SRE is a purified fat-soluble extract of the berry of the saw palmetto palm tree. SRE contains about 85 to 95% by weight fatty acids and sterols, such as capric acid, caprylic acid, caproic acid, lauric acid, myristic acid, isomyristic acid, palmitic acid, stearic acid and oleic acid, and β-sitosterol, stigmasterol, cycloartenol and lupeol. SRE is a complex mix of the saturated and unsaturated fatty acids, ethyl and methyl esters thereof, long chain alcohols in free and esterified form, and free and esterified sterol derivatives.

SRE has been determined in human studies to reduce the activity of 5a-reductase in prostatic tissues as discussed above. Thus, SRE also acts to hinder and block the production of DHT from testosterone. The mechanism of how SRE reduces the activity of 5α-reductase is not fully understood, and it may or may not involve binding of the SRE to the reductase enzyme active site.

The DHT blocker may also comprise a mixture of both the active site binding peptide and SRE.

The pharmaceutical composition may contain the DHT blocker in an amount of, for example, between 5 and 40 percent by weight, preferably between 10 and 30 percent by weight, and more preferably about 20 percent by weight of the composition.

The DHT blockers are preferably encapsulated in liposomes. Liposome encapsulation of the DHT blockers is suitable for either oral or topical application of the pharmaceutical composition. Liposome encapsulation of pharmaceutically active agents is well known in the art. See, for example, U.S. Pat. Nos. 5,567,433, 5,227,170 or 4,752,425, incorporated herein by reference. The type of liposome used for encapsulation is not limited, and any known liposome type may be used. Liposomes of the multilamellar vesicle type are most common.

Any suitable encapsulation method known in the art may be used to encapsulate the DHT blockers in the liposome, for example methods described in the above-referenced patents. For example, encapsulation may be accomplished by the known methods of dehydration/rehydration, solvent-spherule evaporation, etc. In the solvent-spherule evaporation method, the DHT blocker is suspended in a water-in-solvent emulsion (the solvent comprising, for example, chloroform), and the emulsion is mixed with a solvent-in-water solution (the solvent comprising, for example, diethyl ether) containing the lipid precursors of the liposomes. The solvents of the mixed emulsions are then removed. Non-encapsulated DHT blockers are then removed by any suitable separation method such as, for example, fractionation, centrifugation, etc. In the dehydration/rehydration method, preformed liposomes are suspended in a solution such as, for example, a phosphate buffered saline, mixed with a solution or suspension of the DHT blockers, and freeze dried. The freeze dried material is then rehydrated and stirred. Non-encapsulated DHT blockers are removed as above.

Although the liposome for encapsulation may be used without modification, modifying the liposome for tissue specific delivery may be preferable, particularly in oral forms of the composition. For example, in order to facilitate delivery of the DHT blockers to prostatic tissue, the liposome may be modified, or "tagged", with sequences that recognize sites specific to the prostate. Once in the circulatory system (oral) or once having passed through the dermis (topical), the tagged liposome would seek the specific tissue it is tagged for, bind there, and begin releasing the DHT blockers at such desired location.

In the case of delivery to prostatic tissue of a mammal, a compound known as protein specific antigen (PSA) is prevalent in prostatic tissue cell surfaces. Thus, the liposome may be modified or tagged with the recognition sequence for PSA. Once in the system of the mammal, the recognition sequence will act as a beacon to direct the material to the PSA, where it will bind and begin releasing the DHT blockers into the prostatic tissue. General methods to modify liposomes with site specific recognition sequences are known in the art.

An advantage of encapsulating the DHT blockers in liposomes, whether modified or not, is the liposomes ability to encapsulate and protect the active ingredient DHT blockers against degradation within the system of the mammal. Further, the liposomes enable prolonged, slow release of the active ingredient in the prostate, thus properly regulating DHT levels in the prostate over time and maintaining the DHT blockers blocking ability within the prostate between administrations of the composition.

The pharmaceutical composition also preferably includes a pharmaceutically acceptable carrier. Any carriers known in the art for either oral or topical application compositions may be used.

For topical applications, the topical formulation can be, for example, in the form of a solution, suspension, emulsion, gel, or cream of either the oil-in-water or oil-in-oil type, ointment, paste, lotion, shampoo, jelly, or powder. Suitable pharmaceutically acceptable carriers for topical administration may be of any conventional type such as oleaginous bases, for example, cottonseed oil, petrolatum, white petrolatum, mineral oils, silicones, such as dimethyl polysiloxane or methylphenyl polysiloxane, lanolins, polyethylene glycol, glyceryl monostearate, methylcellulose, hydroxymethylcellulose, and the like. The carrier may also include pharmaceutically acceptable surfactants, humectants, wetting agents, dispersing agents, emulsifiers, penetrants, emollients, preservatives, and coloring agents.

For oral applications, the composition may be in the form of a solid or liquid. Solid form preparations include, for example, powders, tablets, dispersible granules and capsules. A solid carrier may be one or more substances such as diluents, flavoring agents, solubilizers, lubricants, suspending agents, binders, tablet disintegrating agents or encapsulating materials. Suitable carrier materials may include, for example, magnesium carbonate, calcium carbonate, sodium bicarbonate, magnesium stearate, calcium stearate, talc, lactose, sugar, pectin, dextrin, starch, tragacanth, cellulose derivatives, methyl cellulose, sodium carboxymethyl cellulose, a low-melting wax, cocoa butter, alginates gelatin polyvinyl pyrrolidone, polyethyl glycols, quaternary ammonium compounds, and the like.

Liquid form preparations include solutions, suspensions, and emulsions. Suitable carriers may include, for example, water, colorants, flavoring agents, stabilizers, and thickening agents. Viscous materials such as natural synthetic gums, resins, methyl cellulose, sodium carboxymethyl cellulose, and other suspending agents known to the pharmaceutical art may also be used.

Preferably, the composition is orally administered to a mammalian patient such as a human male suffering from BPH. More preferably, the oral administration is with the composition in solid form, in particular tablet or capsule form. Solid individual dose forms may have a total weight of, for example, from 0.5 to 1.5 grams, preferably from 0.8 to 1.3 grams, most preferably from 1.0 to 1.2 grams. Oral administration rapidly delivers the DHT blockers to the prostate, and the composition, particularly the encapsulating liposome, protects the DHT blockers during the digestion and circulatory system absorption process of the mammal.

In a preferred embodiment of the invention, the pharmaceutical composition further contains Polygonum multiflorum, commonly also known as fo-ti. Fo-ti is an herb of Chinese origin derived from the root of the Polygonum multiflorum. Studies have revealed that fo-ti increases the activity of superoxide dismutase (SOD), a compound that scavenges cell damaging free radicals from a mammalian system. See, for example, Xiao, "Immunological Aspects of Chinese Medicinal Plants as Antiageing Drugs", Journal of Ethnopharmacology, vol. 38, pps. 167–175 (1993). If included, fo-ti is preferably present in the composition in an amount of from, for example, 1 to 20 percent by weight, preferably 5 to 15 percent by weight, more preferably about 10 percent by weight of the composition. Fo-ti is added to the composition preferably by admixing with the carrier and DHT blockers.

The pharmaceutical composition is administered to a subject either orally or topically as discussed above, preferably orally. The DHT blockers are delivered to the prostate where inhibition of excess DHT production is required. By inhibiting excess DHT production in the prostate, the composition treats and prevents prostate disorders, including BPH.

In order to remove excess DHT from the prostate and maintain the DHT level at a normal base level, the composition is administered to a patient at a daily dose level effective to hinder and block production of excessive DHT in the prostate. Preferably, for example, the pharmaceutical composition is administered at a daily dose level of from 0.5 to 5 grams, more preferably 0.5 to 3.0 grams. The administration may be repeated more than once a day as needed.

The invention has been described in detail with particular reference to preferred embodiments thereof. However, it will be appreciated that those skilled in the art, upon consideration of this disclosure, may make variations and modifications within the spirit and scope of the invention.

What is claimed is:

1. A pharmaceutical composition comprising the dihydrotestosterone blocker *Serenoa repens* and *Polygonum mulitflorum* encapsulated in liposomes.

2. The composition according to claim 1, wherein the dihydrotestosterone blocker is present in an amount ranging from 5 to 40 percent by weight of the composition.

3. The composition according to claim 1, wherein the liposome is tagged with an amino acid recognition sequence permitting tissue specific delivery of the dihydrotestosterone blocker and the *Polygonum multiflorum* to prostate specific antigens in prostate tissue.

4. The composition according to claim 1, wherein the composition is in a solid form of a powder, tablet or capsule.

5. The composition according to claim 4, wherein the solid form has a total weight of 0.5 to 1.5 g.

6. The composition according to claim 1, wherein the *Polygonum multiflorum* is present in an amount ranging from 1 to 20 percent by weight of the composition.

7. A method for inhibiting production of dihydrotestosterone in prostate tissue, comprising administering to a mammal a pharmaceutical composition comprising the dihydrotestosterone blocker *Serenoa repens* and *Polygonum multiform* encapsulated in liposomes, in a prostate dihydrotestosterone inhibiting effective amount.

8. The method according to claim 7, wherein the composition is administered orally.

9. The method acccording to claim 7, wherein the composition is administered topically to a prostate region of the mammal.

10. The method according to claim 7, wherein the composition further comprises a pharmaceutically acceptable carrier.

11. The method according to claim 7, wherein the composition is administered in an amount of from 0.5 to 3.0 grams per day.

12. The method according to claim 7, wherein the composition dihydrotestosterone blocker *Serenoa repens* is present in an amount ranging from 5 to 40 percent by weight of the composition.

13. The method according to claim 7, wherein the liposome is tagged with an amino acid recognition sequence permitting tissue specific delivery of the dihydrotestosterone blocker *Serenoa repens* to prostrate specific antigens in prostate tissue.

14. The method according to claim 7, wherein the *Polygonum multiform* is present in an amount ranging from 1 to 20 percent by weight of the composition.

* * * * *

```
                          SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Ser Ser Asn Ala Thr
1               5

(2) INFORMATION FOR SEQ ID NO:2:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Asn Ser Asn Ala Thr
1               5

(2) INFORMATION FOR SEQ ID NO:3:

(i) SEQUENCE CHARACTERISTICS:
        (A) LENGTH: 5 amino acids
        (B) TYPE: amino acid
        (C) STRANDEDNESS: single
        (D) TOPOLOGY: linear
```

```
        (ii) MOLECULE TYPE: peptide (xi) SEQUENCE DESCRIPTION: SEQ ID NO:3:

Asn Thr Asn Ala Thr
1               5

(2) INFORMATION FOR SEQ ID NO:4:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:4:

Asn Ser Glu Ala Thr
1               5

(2) INFORMATION FOR SEQ ID NO:5:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:5:

Asn Ser Asn Asp Thr
1               5

(2) INFORMATION FOR SEQ ID NO:6:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Asn Ser Asn Ala Ser
1               5

(2) INFORMATION FOR SEQ ID NO:7:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..5
            (D) OTHER INFORMATION: /note= "Xaa is an amino acid
                selected from the group consisting of serine, asparagine,
                alanine, threonine, glutamic acid and aspartic acid."

(xi) SEQUENCE DESCRIPTION: SEQ ID NO:7:

Xaa Xaa Xaa Xaa Xaa
1               5
```